US008801715B2

(12) United States Patent
Sato

(10) Patent No.: US 8,801,715 B2
(45) Date of Patent: Aug. 12, 2014

(54) APPARATUS FOR PREOPERATIVE PLANNING OF ARTIFICIAL KNEE JOINT REPLACEMENT OPERATION AND JIG FOR SUPPORTING OPERATION

(75) Inventor: Takashi Sato, Niigata (JP)

(73) Assignee: Lexi Corporation, Ltd., Tokyo (JP)

(*) Notice: Subject to any disclaimer, the term of this patent is extended or adjusted under 35 U.S.C. 154(b) by 108 days.

(21) Appl. No.: 12/661,980

(22) Filed: Mar. 26, 2010

(65) Prior Publication Data
US 2011/0009868 A1 Jan. 13, 2011

Related U.S. Application Data

(63) Continuation of application No. PCT/JP2008/065900, filed on Sep. 3, 2008.

(30) Foreign Application Priority Data

Sep. 28, 2007 (JP) ................. 2007-256046

(51) Int. Cl.
*A61F 2/46* (2006.01)
*A61B 19/00* (2006.01)
*A61B 17/72* (2006.01)
*A61B 17/17* (2006.01)
*A61B 17/15* (2006.01)

(52) U.S. Cl.
CPC ............ *A61B 19/50* (2013.01); *A61B 2019/501* (2013.01); *A61B 19/56* (2013.01); *A61B 17/72* (2013.01); *A61B 17/1764* (2013.01); *A61B 2019/505* (2013.01); *A61B 2019/508* (2013.01); *A61B 17/155* (2013.01)
USPC ....................................... 606/86 R

(58) Field of Classification Search
CPC ............ A61B 19/50; A61B 2019/50–2019/508
USPC ......................... 606/86 R, 87–89
See application file for complete search history.

(56) References Cited

U.S. PATENT DOCUMENTS

| 4,703,751 A | 11/1987 | Pohl |
| 6,173,200 B1 | 1/2001 | Cooke et al. |
| 2003/0069591 A1* | 4/2003 | Carson et al. ............... 606/130 |

FOREIGN PATENT DOCUMENTS

| JP | 7-136200 A | 5/1995 |
| JP | 2004-008707 | 1/2004 |

(Continued)

OTHER PUBLICATIONS

Aug. 30, 2011 Japanese official action (with English translation) in connection with corresponding Japanese patent application No. 2007-256046.
International Search report issued Dec. 22, 2008 in connection with International Application No. PCT/JP2008/065900, including English language translation.
Japanese official action dated Apr. 9, 2013, and English-language translation thereof, in connection with corresponding Japanese patent application No. JP2005-517470.

(Continued)

*Primary Examiner* — Sameh Boles
(74) *Attorney, Agent, or Firm* — John P. White; Cooper & Dunham LLP

(57) ABSTRACT

Methods and apparatuses for displaying images are provided which input two-dimensional tomographic images of the lower limb including the knee joint, display three-dimensional images of the femur and the tibia including the knee joint from the image input, determine an artificial joint to be replaced from the three-dimensional images of each knee joint of the femur and tibia, and determine various parameters used in an artificial knee joint replacement operation using an alignment rod in the marrow to be inserted into the femur based on the artificial joint and reference points of the knee joint determined when determining a femur side artificial joint.

1 Claim, 14 Drawing Sheets

(56) References Cited

FOREIGN PATENT DOCUMENTS

| | | |
|---|---|---|
| JP | 2004-527286 | 9/2004 |
| JP | 2005-13737 | 1/2005 |
| JP | 2005-517470 | 6/2005 |
| JP | 2005-253969 A | 9/2005 |
| TW | 558689 | 10/2003 |
| WO | WO 2005/099636 A1 | 10/2005 |
| WO | WO2006/092600 | 9/2006 |

OTHER PUBLICATIONS

Japanese official action dated Aug. 20, 2013 in connection with corresponding Japanese patent application No. JP2011-239198 (English translation thereof enclosed herewith).

Taiwanese official action dated Sep. 4, 2013 in connection with corresponding Taiwanese Application No. 97135785 (English translation thereof enclosed herewith).

Jan. 30, 2014 Chinese official action in connection with corresponding Chinese patent application No. 201210134589.5.

* cited by examiner

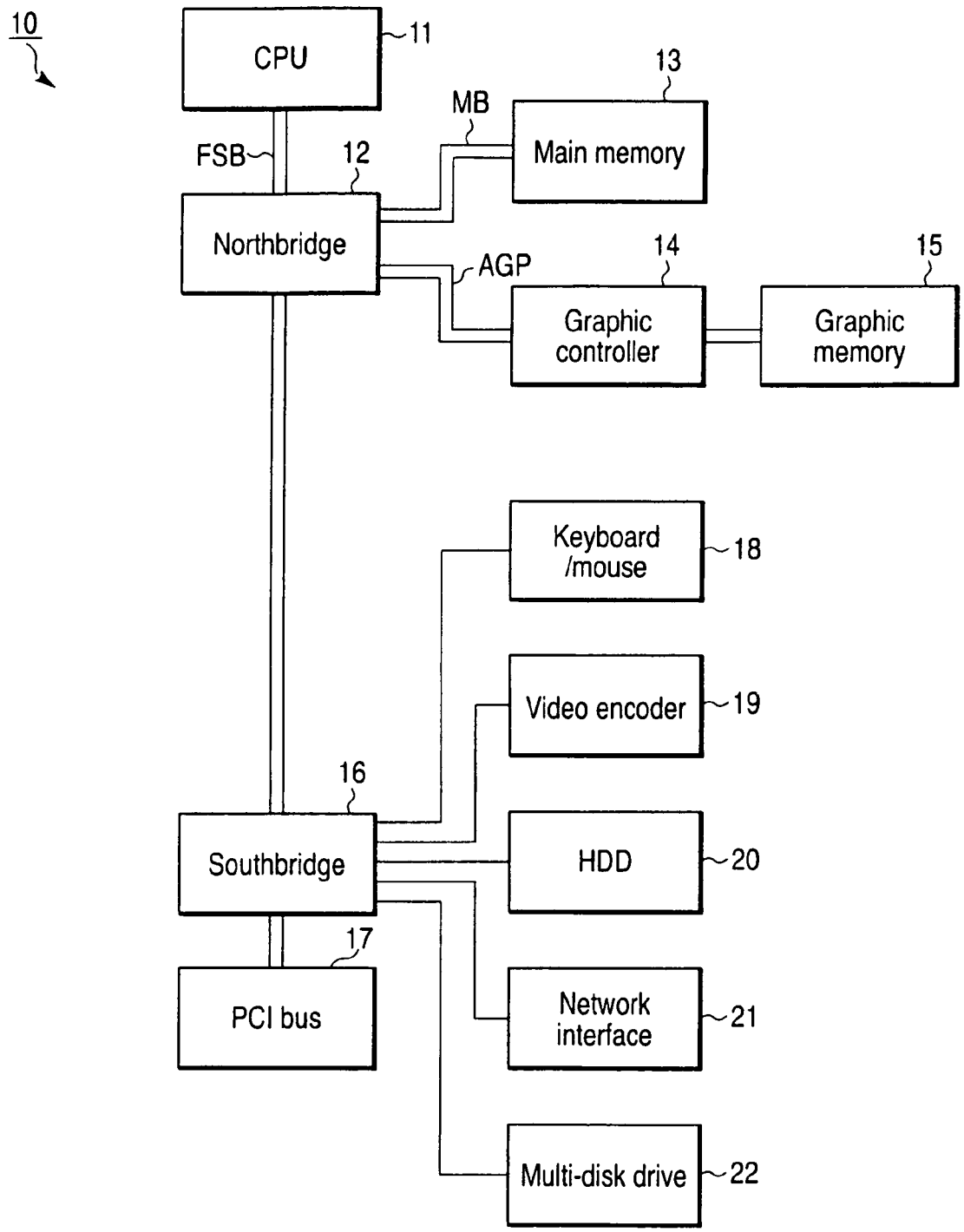
F I G. 1

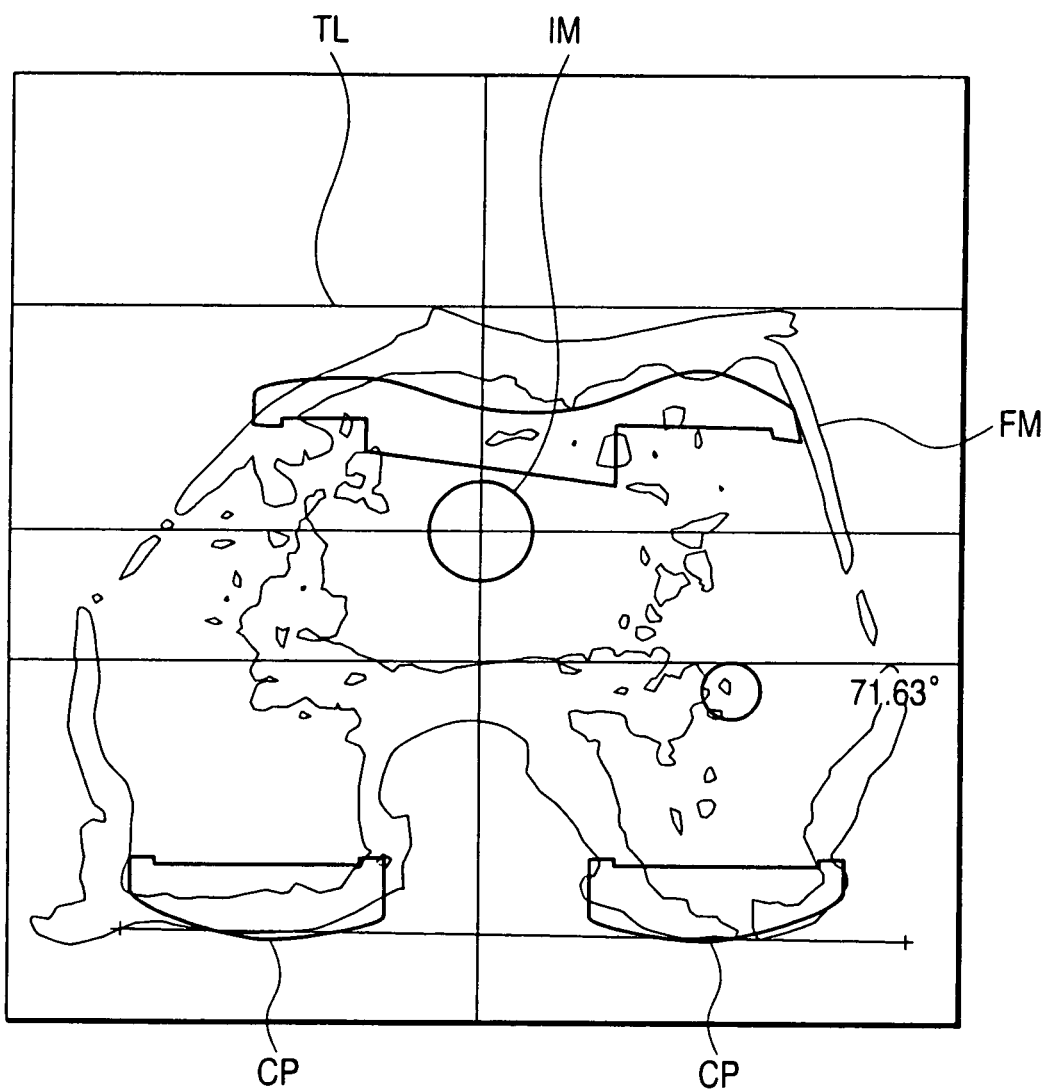
F I G. 8

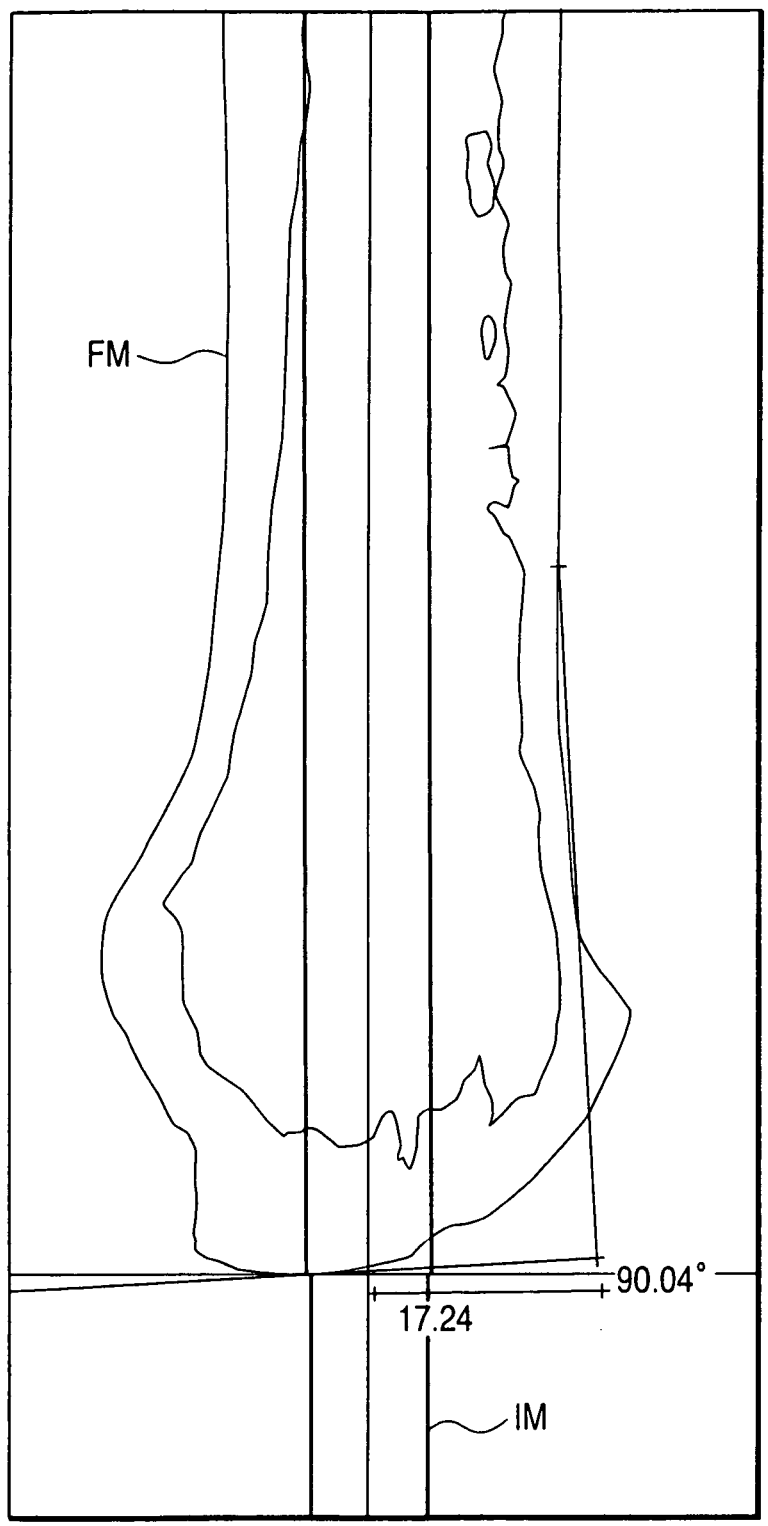
F I G. 9

| Data for bone cutting | | |
|---|---|---|
| | Extent of bone cutting by each site | Gauge-measured value |
| Distal medial side of femur | 7.6 mm | 0.0 mm |
| Distal lateral side of femur | 7.4 mm | 0.2 mm |
| Medial femoral posterior condylar | 7.3 mm | 7.3 mm |
| Lateral femoral posterior condylar | 7.4 mm | 7.4 mm |
| Proximal medial side of tibia | 7.2 mm | 7.2 mm |
| Proximal lateral side of tibia | 8.7 mm | 8.7 mm |
| Functional axis angle 3D of rod IM Coronal | Varus 7.5 deg | |
| Sagittal | Extension 1.0 deg | |
| Insertion depth of rod IM | | |
| 7inch | 0.7 mm | |
| 9inch | 51.5 mm | |

FIG. 10

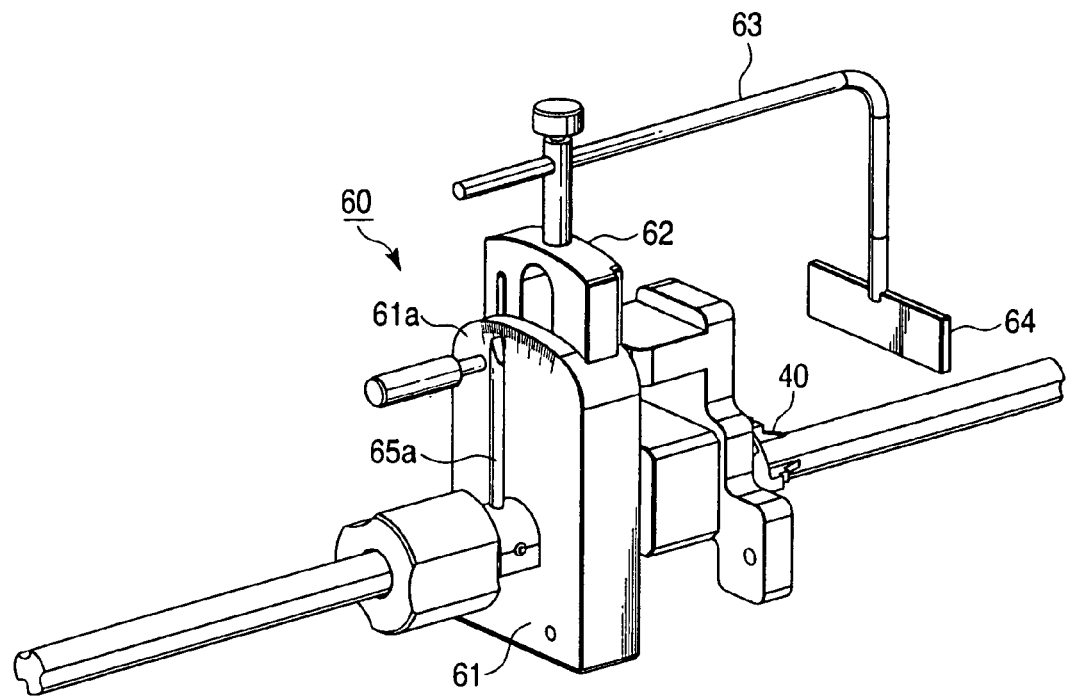
F I G. 14A
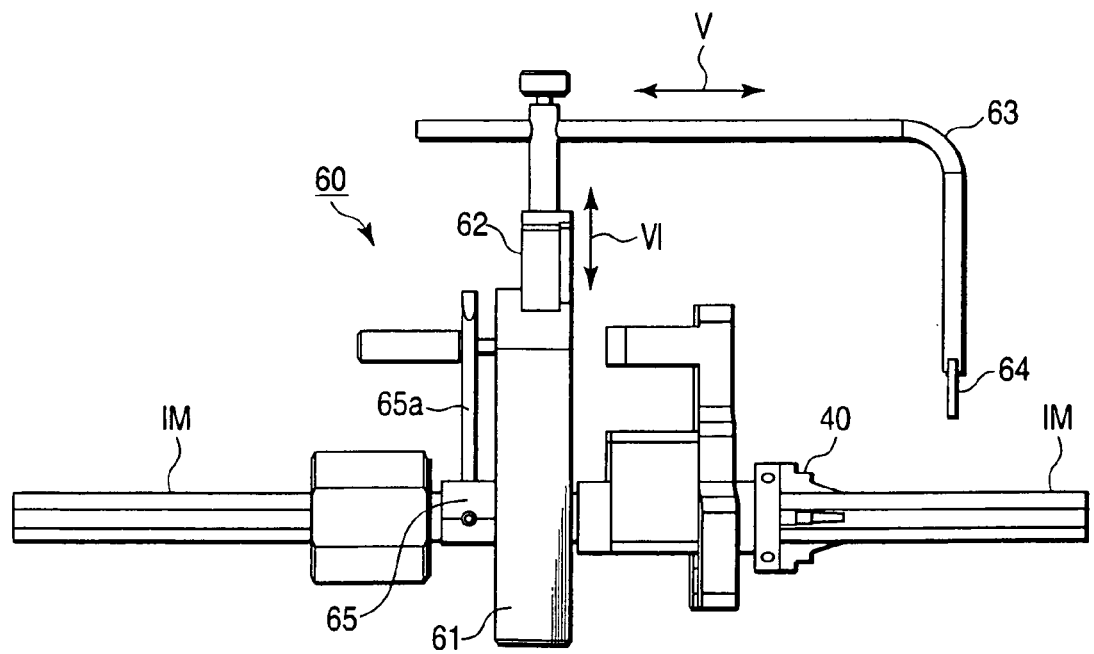
F I G. 14B

APPARATUS FOR PREOPERATIVE PLANNING OF ARTIFICIAL KNEE JOINT REPLACEMENT OPERATION AND JIG FOR SUPPORTING OPERATION

CROSS REFERENCE TO RELATED APPLICATIONS

This is a Continuation Application of PCT Application No. PCT/JP2008/065900, filed Sep. 3, 2008, which was published under PCT Article 21(2) in Japanese.

This application is based upon and claims the benefit of priority from prior Japanese Patent Application No. 2007-256046, filed Sep. 28, 2007, the entire contents of which are incorporated herein by reference.

BACKGROUND OF THE INVENTION

1. Field of the Invention

The present invention relates to an apparatus for preoperative planning of an artificial knee joint replacement operation and a jig for supporting the operation in order to plan an artificial knee joint replacement operation for the knee of the human body using a tomographic image for medical use and perform the operation.

2. Description of the Related Art

In recent years, tomographic image diagnostic apparatuses such as X-ray CT scanners and MRI apparatuses have spread. The use of these apparatuses allows for the observation and diagnosis of parts of the body. In contrast, osteoarthritis of the knee has been increasing with aging not only in Japan but also in other countries. The operation in which the affected part of the knee joint is replaced with an artificial joint made of metal or ceramics is wide spread today. In the artificial knee joint replacement, the important consideration is that an artificial joint having the optimal shape and size for a patient is placed at the optimal angle and the optimal position.

As the operation planning for that, a template in which a two-dimensional shape of the artificial joint is drawn on a transparent film is superimposed on a simple X-ray image from the two-dimensional front and lateral side. Alternatively, the size, position, and orientation for placing the artificial joint as well as the extent and position of bone cutting are measured on the simple X-ray image film using a ruler at present.

In the manual measurement using the template and the ruler on the basis of the two-dimensional simple X-ray image, the measurement accuracy of the size and position is insufficient. In addition, it is difficult to figure out the installation position and the extent of bone cutting three-dimensionally and quantitatively. Therefore, considerable experience and accumulation of technique are needed.

Consequently, it has been difficult for all the orthopedists to immediately perform the exact and highly accurate operation planning and operation. Particularly, the accuracy as to the installation position and orientation of the artificial joint has a great effect on the durability of the artificial joint. In addition, the accuracy is the most important element to allow patients after the operation to go about their normal lives without ill effects every day for a long period of 10 or 20 years.

In the method using the two-dimensional template, it has been difficult to perform such processing.

On the other hand; in order to support an operator so that the operator can easily find an ideal bone cutting surface of the tibia in the artificial knee joint replacement, a technique which performs the three-dimensional simulation using the personal computer is considered as shown below (for example, Patent document 1: Jpn. Pat. Appln. KOKAI Publication No. 2004-008707).

Conventionally, when the installation angle of the component of the femur side (artificial joint) is determined during the operation, the method of using an alignment rod in the marrow (hereinafter referred to as a "rod in the marrow") which is inserted into the bone is generally used. The angle of distal bone cutting surface which specifies the varus-valgus angle and the flexion-extension angle of the component is determined from a difference between the axis of the rod and the mechanical axis of the femur by inserting the rod in the marrow.

At this time, the angle of the rod in the marrow can be adjusted to target installation angle of the component to some extent with an instrument in determining the varus-valgus angle. However, the flexion-extension angle cannot be adjusted and is completely dependent on the insertion angle of the rod in the marrow. In other words, this means that the installation angle of the femur component is dependent on the insertion angle of the rod in the marrow.

In the method of using the rod in the marrow, since there are differences in the bone shape among individuals, the insertion angle of the rod in the marrow varies depending on each case. Thus, it is difficult to reliably form a distal bone cutting surface at a prearranged angle.

Further, the installation angle in the rotation direction of the femur component which is very important in clinical practice is determined in the distal bone cutting surface. Thus, when the distal bone cutting surface in itself is inaccurate, the rotation angle is inevitably inaccurate.

In this respect, there is no description about the failure caused by the use of the rod in the marrow at the femur side in Patent document 1 in which the technique at the side of tibia is described.

BRIEF SUMMARY OF THE INVENTION

An objective of the present invention is to provide an apparatus for preoperative planning of an artificial knee joint replacement operation and a jig for supporting the operation in which the position and angle of the distal bone cutting surface can be accurately determined using the alignment rod in the marrow while differences in patients are properly reflected and the exact surgery can be performed by recreating the content determined from the reference points of the femur knee joint using a jig for exclusive use which is attached to the alignment rod in the marrow during the operation.

According to a first aspect of the present invention, there is provided an apparatus for preoperative planning of an artificial knee joint replacement operation, comprising: means for inputting an image which inputs a two-dimensional tomographic image of the lower limb including the knee joint; means for reconstructing an image which reconstructs a three-dimensional image of the femur and tibia from the image input by the means for inputting an image; means for determining femur side artificial joint which determines the artificial joint to be replaced from the three-dimensional image of the knee joint of the femur obtained by the means for reconstructing an image; means for determining tibia side artificial joint which determines the artificial joint to be replaced from the three-dimensional image of the knee joint of the tibia obtained by the means for reconstructing an image; and means for parameter determination which determines various parameters used in artificial knee joint replacement using an alignment rod in the marrow which is inserted into the femur based on the artificial joint determined by the means for determining femur side artificial joint and a reference point of the knee joint.

According to a second aspect of the present invention, there is provided a jig for an artificial knee joint replacement operation, comprising: a contact portion which contacts the reference point of the knee joint of the femur; a mounting portion which mounts the alignment rod in the marrow to be inserted into the marrow of the femur; and an arm portion which connects the contact portion with the mounting portion and can adjust the attaching position and angle of the mounting portion.

According to a third aspect of the present invention, there is provided a jig for an artificial knee joint replacement operation, comprising: a contact portion which contacts the reference point of the knee joint of the femur; a mounting portion which mounts the alignment rod in the marrow to be inserted into the marrow of the femur; and a connection portion which connects the contact portion with the mounting portion and can adjust the attaching angel of an external jig which is mounted on the alignment rod in the marrow.

BRIEF DESCRIPTION OF THE SEVERAL VIEWS OF THE DRAWING

FIG. 1 is a block diagram illustrating a hardware configuration of the personal computer in which a program for preoperative planning of an artificial knee joint replacement operation is installed.

FIG. 8 is a cross-sectional view of the bone in accordance with the position in FIG. 7.

FIG. 9 is a diagram illustrating the offset between a forward tangent and the coordinate center of the rod.

FIG. 10 is a diagram illustrating the case where some of the stored various parameters according to the embodiment are read and are displayed on a display screen.

FIG. 14A is a perspective view illustrating the appearance structure of another jig for determining the rotation angle.

FIG. 14B is a side view illustrating the appearance structure of another jig for determining the rotation angle.

DETAILED DESCRIPTION OF THE INVENTION

Figure 2:
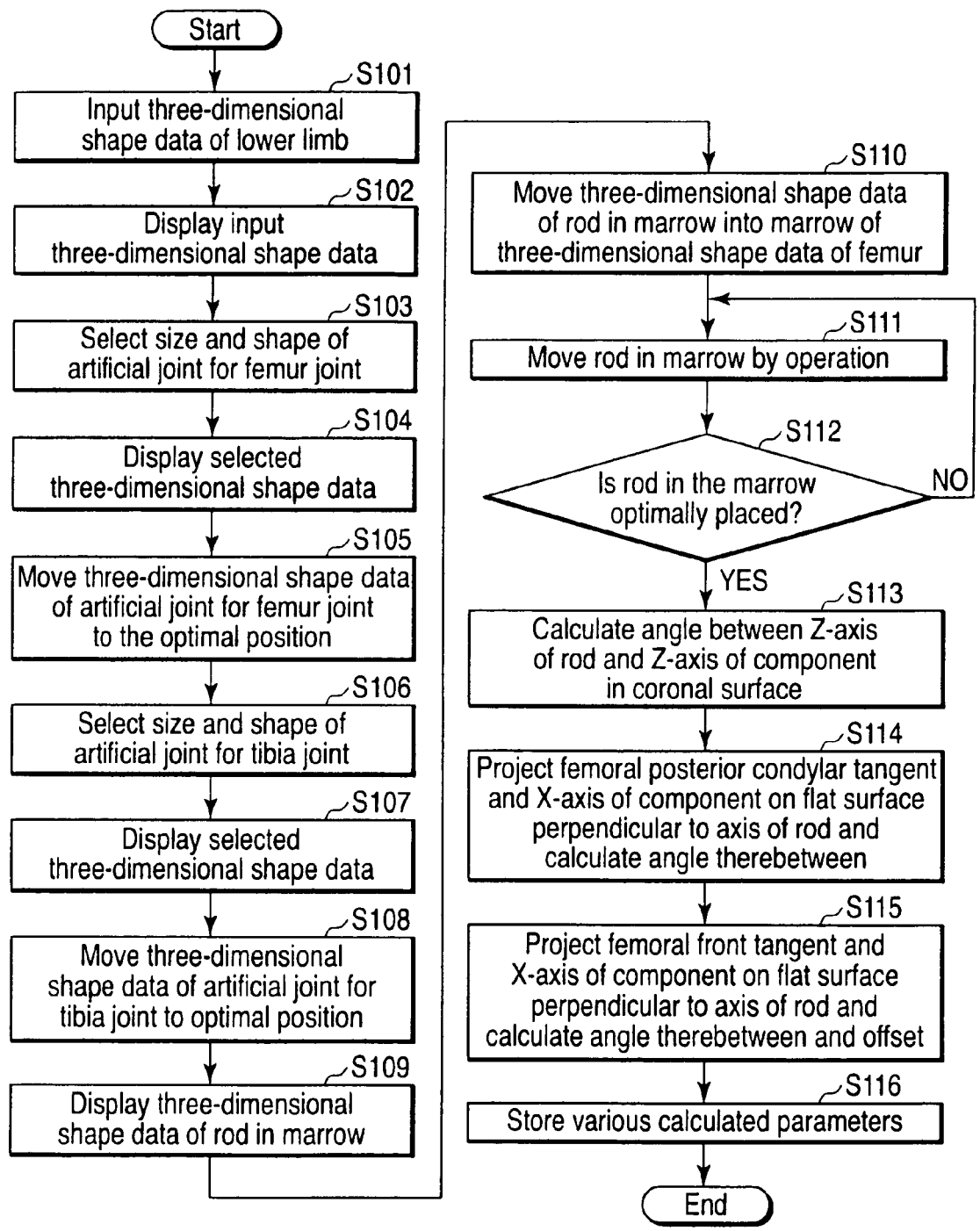
FIG. 2 is a flowchart illustrating the content for processing of the program for preoperative planning.

Hereinafter, one embodiment of the present invention will be described with reference to drawings.

FIG. 1 is a hardware configuration of a personal computer (hereinafter referred to as a "PC") 10 in which a program for preoperative planning of an artificial knee joint replacement operation is installed. A CPU 11 which manages various processing controls is connected to a northbridge 12 via a front side bus (FSB).

The northbridge 12 is further connected to a main memory 13 via a memory bus (MB) and is connected to a graphic controller 14 and a graphic memory 15 via an AGP graphics interface. In addition, it is also connected to a southbridge 16 and mainly performs input-output control thereof.

The southbridge 16 is connected to a PCI bus 17, a keyboard/mouse 18, a video encoder 19, a hard disk drive (HDD) 20, a network interface 21, and a multi-disk drive 22 and mainly performs input-output control of these peripheral circuits and the northbridge 12.

An operating system (OS), various application programs, various data files, as well as the program for preoperative planning of an artificial knee joint replacement operation, and data of the shapes of the rod in the marrow and various jigs associated with it and are pre-installed in the hard disk drive 20.

In this regard, the video encoder 19 generates an RGB video signal which is an image signal of an analog value from an image signal of a given digital value, outputs it, and then drives a display portion constituted of a color thin-film transistor (TFT) liquid crystal display panel (not shown herein) to display.

The multi-disk drive 22 can reproduce and record an optical disk media in accordance with for example, the Compact Disc (CD) standard and the Digital Versatile Disc (DVD) standard. The three-dimensional shape data of the patient's lower limb can be input into the hard disk drive 20 by reproducing and reading the optical disk media in which an X-ray of the patient, a laminagram captured by X-ray computed tomography, or the like are recorded in order to record the data therein.

In this regard, respective elements constituting a PC 10 are generally well-known techniques and therefore the description will not be repeated here.

Subsequently, the operation of the embodiment described above will be described.

FIG. 2 shows the content of processing of the present invention which is mainly performed by the CPU 11 when a medical practitioner who is the user of the PC 10 starts the program for preoperative planning stored in the hard disk drive 13.

In executing the program for preoperative planning, the three-dimensional bone shape data of a patient's lower limb produced from a two-dimensional tomographic image data slice captured by an X-ray CT scanner or an MRI apparatus is read and stored in the hard disk drive 20.

In this regard, as for the three-dimensional bone shape data of the lower limb which is produced based on a series of two-dimensional tomographic image of the lower limb of the human body on the program, major landmarks such as the center of the bone head, the center of the posterior condylar of the knee joint, the tibia intercondylar eminence, or the medial or lateral border points of the tibia distal articular surface are set as three-dimensional reference points. The coordinate system of the femur and tibia is set using those reference points. It does not matter whether a three-dimensional positional relationship between the femur and tibia, namely, alignment in itself is in a standing position or a decubitus position.

Although an absolute definition is not particularly necessary in the coordinate system, the following coordinate system is used as a matter of convenience herein. With reference to the femur coordinate system, the center of the straight line connecting the center of the medial and lateral posterior condylar portions is the origin. The rightward of the human body along the straight line is the X-axis. The vector product of a vector connecting the origin with the center of the bone head and a vector of the X-axis is the Y-axis. Therefore, as for the Y-axis, the front side of the body is defined as positive. The Z-axis will be determined from the X-axis and the Y-axis.

With reference to the tibia coordinate system, the line connecting the center of the line connecting the medial or lateral border points of the tibia distal articular surface with the center of the tibia intercondylar eminence is the Z-axis. The proximal direction, namely, the upper direction is defined as positive. The Y-axis is the line connecting the tibia posterior cruciate ligament attachment site with the tuberositas tibiae. The front side of the body is defined as positive. The X-axis is determined from Y-axis and the Z-axis.

Further, the three-dimensional shape data of the artificial joint is separately prepared and stored in the hard disk device 20. As with the femur and tibia, original coordinate systems of a femur prosthesis and a tibia prosthesis are respectively set.

Specifically, in the femur prosthesis, for example, a proximal direction or a vertical direction is the Z-axis, the direction of the front side of the body is the Y-axis, and the rightward relative to the body side is the X-axis. However, it is not necessary that the coordinate axis is absolutely placed in such a manner and another definition can be used. The coordinate system as to the tibia prosthesis is defined in the same manner.

Therefore, when the program for preoperative planning of FIG. 2 is started, a graphical user interface (GUI) is displayed. Then, the three-dimension shape data in the desired standing or decubitus position of the lower limb which is displayed on the GUI is selected.

This process is performed by designating the folder used in the general PC program in which the three-dimensional shape data of the lower limb is stored. Further, as for the three-dimensional shape data of the femur and the three-dimensional shape data of the tibia, the three-dimensional positional relationship (three-dimensional alignment) between the three-dimensional shape data of the femur and the three-dimensional shape data of the tibia in the standing position in the loaded state and/or the decubitus position in the non-loaded state is correctly placed in advance.

Subsequently, the selected three-dimensional shape data of the femur of the lower limb is read into the main memory 13 from the folder of the hard disk drive 20 (step S101). The image obtained by observing the three-dimensional shape data from an appropriate viewpoint is displayed on the display screen (step S102). In the display, the three-dimensional image which is perspectively projected or the three-dimensional shape data can be two-dimensionally displayed in the cross-section in the flat surface parallel to the coordinate axis.

Then, the three-dimensional shape data of the artificial joint for the femur joint with an appropriate size and shape is selected (step 103). The data is read from the hard disk drive 20 and displayed on the display screen (step 104).

Then, the three-dimensional shape data of the artificial joint for the femur is appropriately moved in parallel and rotationally moved by operation of the keyboard/mouse 18 and placed in the optimal position to the three-dimensional shape data of the femur.

The term "optimal position" used herein is a position which is optimal in orthopedic surgery and proposed by societies and each of the artificial joint manufacturers. Further, it is the relative installed position of the artificial joint for each of the femur and tibia. This position is the optimal position to place the artificial joint during the operation and the bone is cut based on the installed position (step S105).

More specifically, it is generally recommended that the distal articular surface of the femur component (artificial joint) and the proximal articular surface of the tibia component are perpendicular to the mechanical axis on the coronal section. However, as for the angle (flexion-extension angle) on the sagittal section, there is no constant consensus in both components. Thus, the medical practitioner needs to decide the angle properly in accordance with the shape of the joint of individual patients. Further, as for the rotation angle in the axial direction, it is recommended that the X-axis of a femur component be set parallel to the transepicondylar axis (hereinafter referred to as the TEA). The medical practitioner who is the user of the program may set the installed position in an interactive mode on the program. The automatable portion may be automatically placed using the reference points.

Then, the three-dimension shape data of the artificial joint for the tibia joint with an appropriate size is selected (step S106). The date is read from the hard disk drive 20 and displayed on the display screen (step S107).

Then, as with the side of femur described above, the three-dimensional shape data of the artificial joint for the tibia is appropriately moved in parallel and rotationally moved by operation of the keyboard/mouse 18 and placed in the optimal position to the three-dimensional shape data of the tibia (step S108).

The medical practitioner who is the user of the program may set the installed position in an interactive mode on the program. The automatable portion may be automatically placed using the reference points.

As described above, in the present embodiment, respective artificial joints are easily placed in three-dimensionally ideal positions for bones of lower limb and thus the quantitive installation parameter and the bone cutting parameter can be obtained.

Then, the three-dimensional shape data of the rod in the marrow which is pre-installed is read from the hard disk drive 20 (step S109). The data is displayed on the display screen (step S110).

A mark indicating the depth is pre-installed into the three-dimensional shape data of the rod in the marrow. The coordinate system of the rod is defined. The long axis is the Z-axis and the front side is the Y-axis. The vector product of the Y-axis and the Z-axis is the X-axis. The coordinate system is set as a matter of convenience and another definition may be used.

The three-dimensional shape data of the rod in the marrow which is read can be parallelly moved to distal and proximal, medial or lateral side, and forward and backward. The data can be rotated in the internal-external rotational direction, in the varus-valgus direction, or in the flexion-extension direction.

On the display screen, the three-dimensional shape data of the alignment rod in the marrow is rotationally moved and moved in parallel by operation of the keyboard/mouse 18 and then appropriately placed in the marrow of the three-dimensional shape data of the femur (step S111).

That is, based on the shape data of the femur, the rod in the marrow is placed in an appropriate position in the marrow. In other words, the insertion position, orientation, and depth of the rod in the marrow are three-dimensionally arranged at an optimal angle and position. The term "optimal angle and position" used herein is the angle and position in which the insertion point, varus-valgus angle, and insertion depth are adjusted so that the insertion depth in the marrow is as large as practicable under the condition according to the flexion-extension installation angle of the selected artificial joint.

In fact, the position is that the Z-axis of the rod in the marrow exists in the flat surface parallel to the XZ flat surface as described hereinafter. As a result, when the rotation angle is accurately set, the angle of the rod in the marrow is matched with the artificial joint in the flexion-extensional direction.

Figure 3:
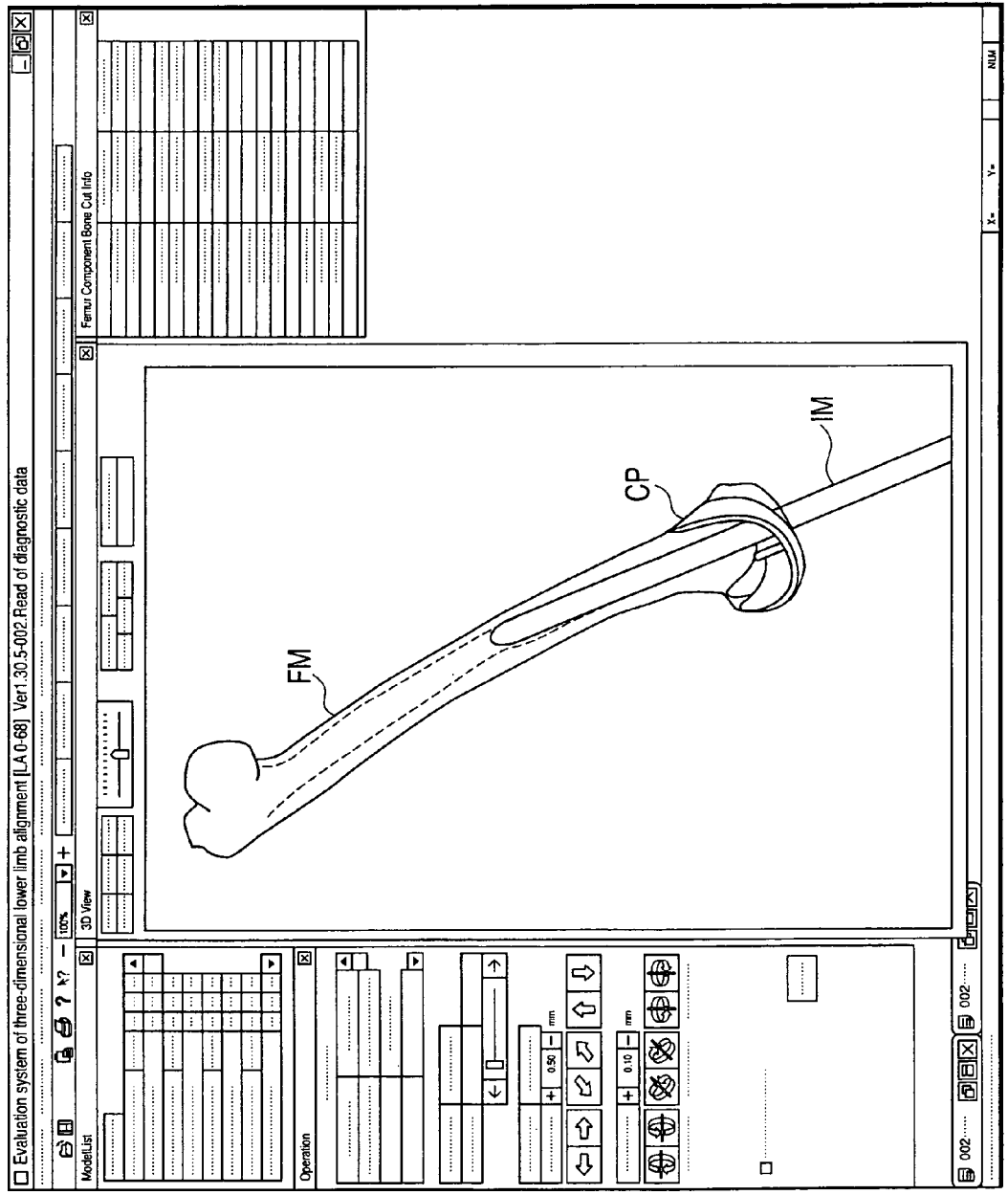
FIG. 3 is a diagram illustrating a three-dimensional shape data of the femur, artificial joint, and rod in the marrow are displayed on a display screen.

FIG. 3 is a diagram illustrating a three-dimensional shape data of the femur, artificial joint, and rod in the marrow are displayed on a display screen at this time. FIG. 3 shows the state in which the optimal position of an artificial joint CP is selected and placed in a knee joint part of a femur FM and a rod in the marrow IM is inserted into the femur FM.

Then, the three-dimensional shape data of the rod in the marrow IM is moved to the femur FM and the artificial joint CP by operation of the keyboard/mouse 18 (step S111). Then, the end of the placement into the optimal position is determined by, for example, the presence or absence of the instruction of a "determination" button during GUI display (step S112).

Otherwise, the process is returned to the processing of step S111 and the position movement of the rod in the marrow IM by the operation is repeated. It is waited till the rod in the marrow IM is moved to the optimal position in the marrow of the femur FM.

As described above, in the optimal placement of the rod in the marrow IM, the optimal placement of the rod in the marrow IM means that the angle and position according to the installation angle of the artificial joint CP to be intended, namely, the Z-axis matched with the axis of the rod in the marrow IM, becomes parallel to the XZ in-plane of the coordinate system of the artificial joint CP for femur. When the medical practitioner (i.e., the user) repeats the processing of steps S111 and S112 on the program, the optimal placement is achieved.

Figure 4:
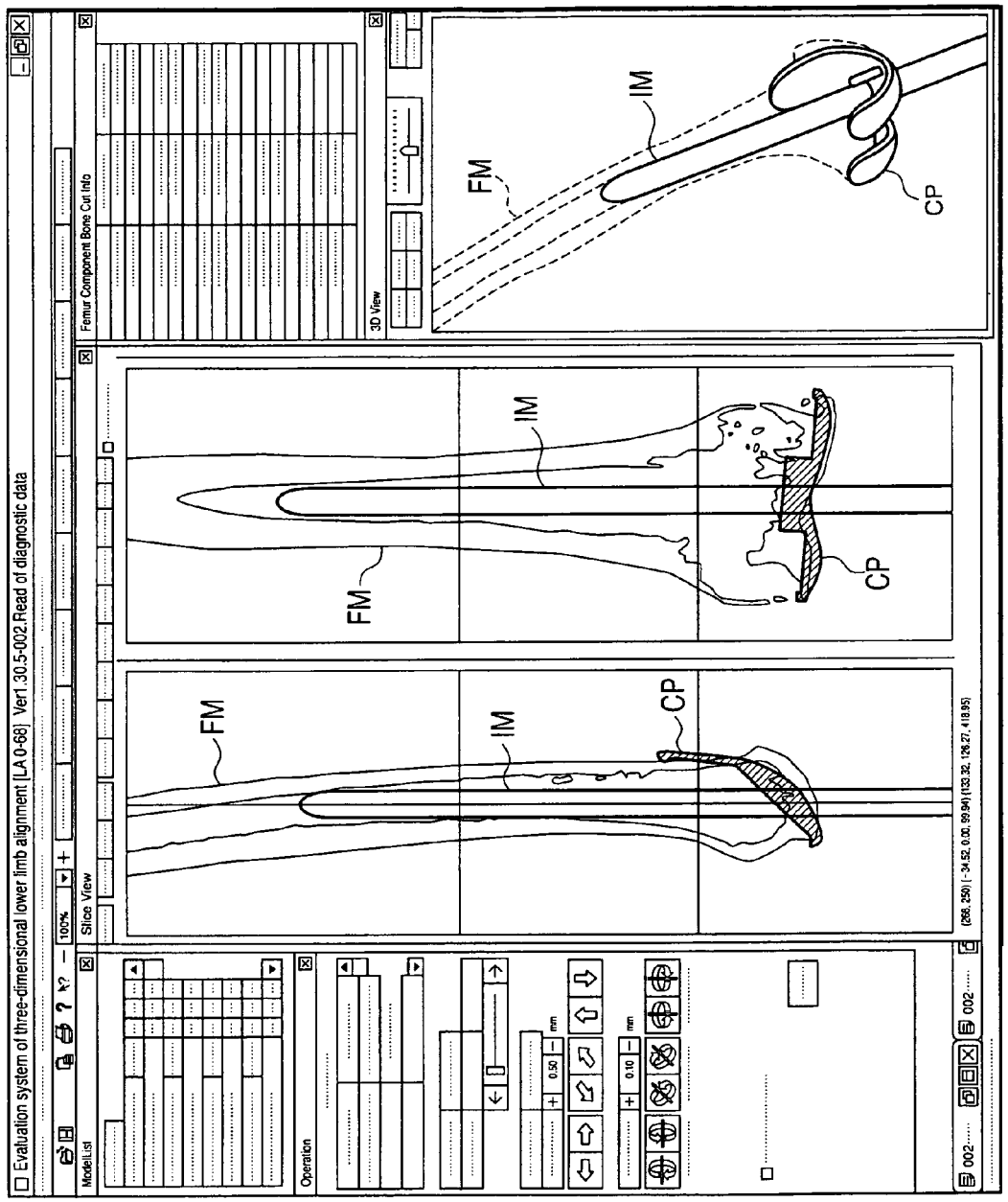
FIG. 4 is a diagram illustrating a three-dimensional shape data of the femur, artificial joint, and rod in the marrow are displayed on a display screen.
Figure 5:
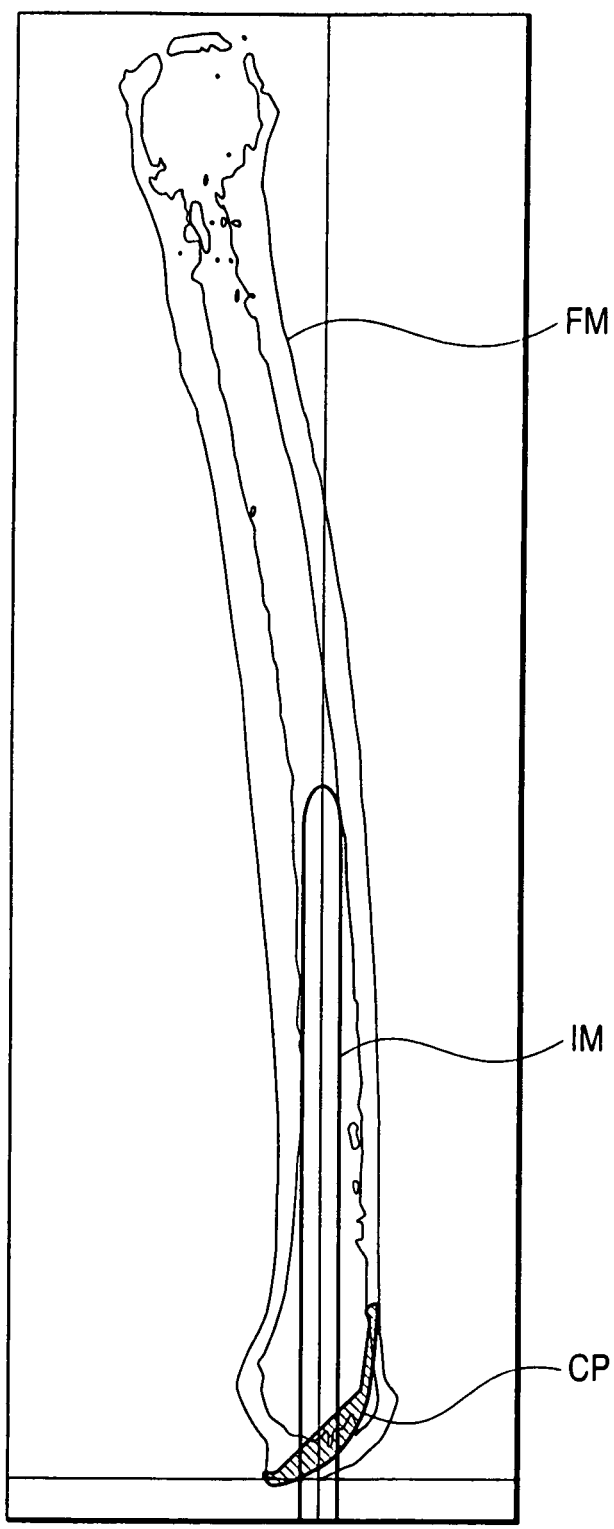
FIG. 5 is a diagram illustrating an image in which the position of the rod in the marrow against the femur and artificial joint is displayed.

FIGS. 4 and 5 exemplify an image in which the position of the rod in the marrow IM for the femur FM and the artificial joint CP is displayed along the two-dimensional flat surface based on the three-dimensional shape data by switching the displayed state in the process of obtaining the proper arrangement.

In FIG. 4, the cross section observed from the side surface passing through the central axis (Z-axis) of the rod in the marrow IM in the screen and the cross section observed from the front side are shown together with the original three-dimensional shape.

In FIG. 5, the positional relationship between the artificial joint CP and the rod in the marrow IM based on the whole femur FM is extracted from the display screen in the GUI environment shown in FIGS. 3 and 4, which is exemplified.

FIG. 5 shows the state in which the rod in the marrow IM in the curved marrow of the femur FM is inserted into the innermost part (upper part in the human body in a standing position).

Thus, the optimal placement state of the rod in the marrow IM is obtained. When the optimal placement is instructed by the user, this is determined in step S111 and the angle (varus-valgus angle) between the Z-axis (i.e., the axis of the rod in the marrow IM) and the Z-axis of the artificial joint CP is calculated in the coronal surface (step S113).

Figure 6:
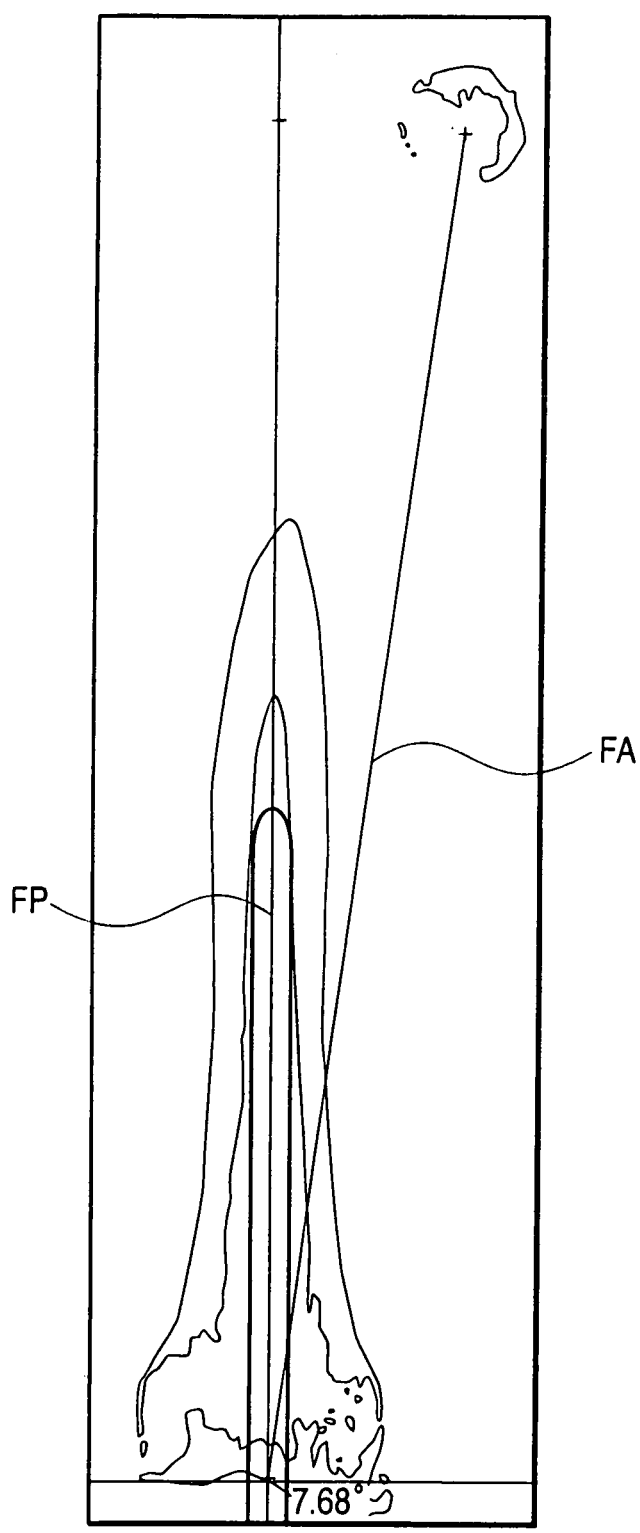
FIG. 6 is a diagram illustrating the angle between a mechanical axis of femur and a distal bone axis.

FIG. 6 exemplifies the varus-valgus angle and corresponds to the angle between a mechanical axis FA and a distal bone axis FP in the femur coordinate system. Usually, the angle is about 7 degrees (7.68 degrees in the drawing). It may vary more greatly depending on individual differences.

Subsequently, the rotation angle is determined. The femoral posterior condylar tangent which are referenced during the operation and the X-axis of the artificial joint CP are projected on the flat surface perpendicular to the axis of the rod in the marrow IM. The angle between them (hereinafter referred to as the "posterior condylar tangent-artificial joint angle") is calculated (step S114).

The medical practitioner who is the user of the program can figure out which side and how many degrees the X-axis of the artificial joint CP should be rotated around the rod in the marrow IM from the state parallel to the axis of the posterior condylar tangent during the operation.

As preoperative preparation in another method for determining the rotation angle, the cross-sectional image of the bone in the proximal part within a few millimeters from the proximal edge of the patellofemoral joint is displayed on the flat surface (this is a flat surface "R") perpendicular to the axis of the rod in the marrow IM. The tangent of the two points in the bimodal portion of the front cortex is determined by digitizing two points. The angle (hereinafter referred to as the "front tangent-artificial joint angle") between the tangent and the X-axis of the artificial joint is determined. The offset distance from the coordinate center of rod to the flat surface R is calculated (step S115).

Figure 7:
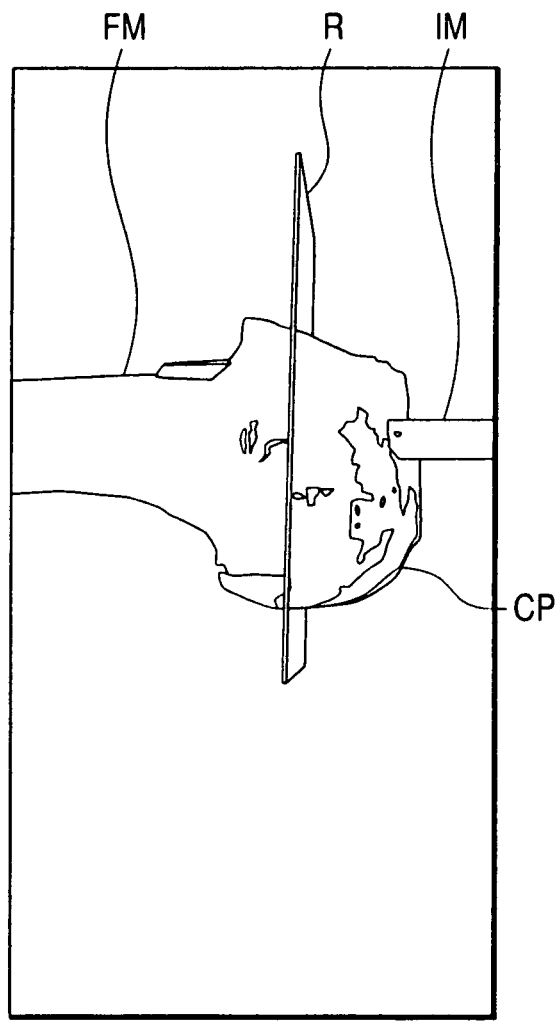
FIG. 7 is a diagram illustrating the position of the bone section of the patellofemoral joint along the flat surface perpendicular to an axis of the rod in the marrow.

FIG. 7 shows the flat surface R. FIG. 8 is a front tangent TL on the flat surface R. The position of the front tangent TL is located at the side which is directly visible during the operation. Since the position is not affected by the presence of cartilage, it can be used as one of the reference points which can be recognized very easily.

FIG. 9 is a diagram illustrating the offset (17.24 mm in the figure) between the front tangent TL and the coordinate center of the rod.

As described above, the planning for an artificial joint replacement operation before the operation is carried out and various necessary parameters are calculated and stored (step S116). Thus, the optimal bone cutting can be performed using these various parameters at the time of the actual operation using a surgical instrument.

FIG. 10 is a diagram illustrating the case where some of the various stored parameters are read and are displayed on a display screen. That is, the parameter values which should be calculated by the program for preoperative planning includes the followings:

(1) the data of the insertion point of the rod in the marrow: ΔY value from the flat portion (approximated by the flat surface) within about 30 mm from the proximal edge of the femoropatellar joint at the front portion of the femur distal portion for placing the target device to the insertion point of the rod in the marrow, namely, the distance when projected on the YZ flat surface of the femur coordinate system;

(2) the insertion depth of the rod, namely, the length from the insertion point to the tip of the rod;

(3) the rotation angle of the X-axis of the rod based on the posterior condylar axis (PCA) of the femur and the front tangent-artificial joint angle;

(4) the angle (coronal surface) between the Z-axis of the rod and the Z-axis of the component (three-dimensional mechanical axis); and (5) the angle (sagittal surface) between the Z-axis of the rod and the Z-axis of the component (three-dimensional mechanical axis).

At the time of the actual operation using a surgical instrument, the jig referred to as the target device is used as a first jig for the flat portion located proximal to the upper end of the patellar surface of femur in order to determine the insertion point of the rod in the marrow.

Figure 11A:
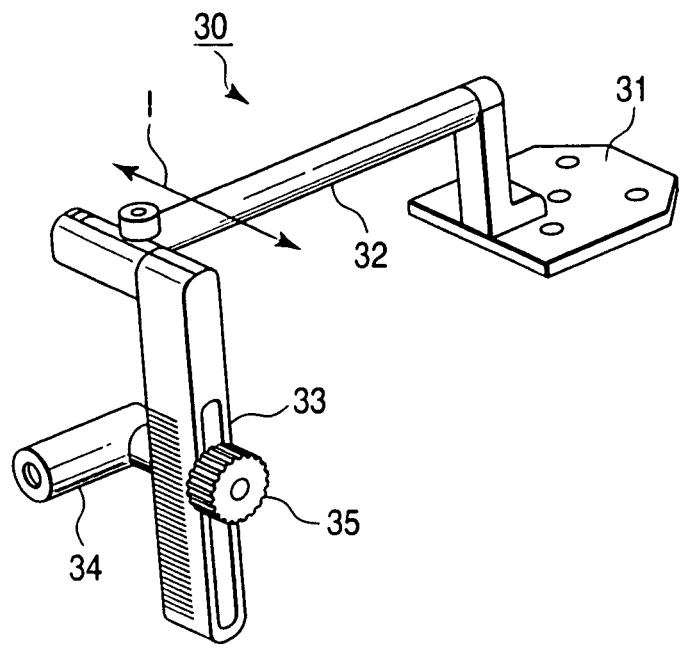
FIG. 11A is a perspective view illustrating the appearance structure of a target device.
Figure 11B:
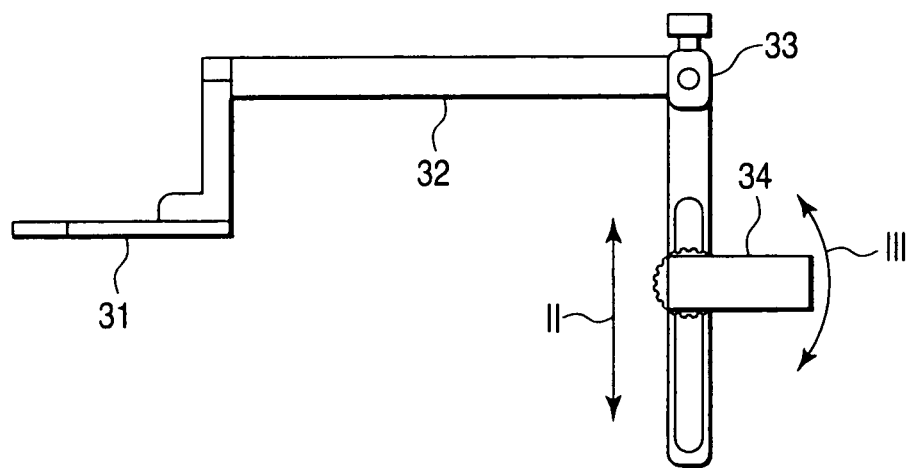
FIG. 11B is a side view illustrating the appearance structure of the target device.

FIGS. 11A and 11B illustrate the shape of a target device 30 which is used at this time. FIG. 11A is a perspective view and FIG. 11B is a side view. The target device 30 includes a contact portion 31, an arm portion 32, and a mounting portion 33.

The contact portion 31 is the site which contacts the front tangent. The arm portion 32 is fixedly connected to the contact portion 31. Further, the mounting portion 33, which can be moved parallel to arrow I in the drawing which becomes perpendicular to the axis of the arm portion 32 and becomes parallel to the front tangent, is attached to the tip of the arm portion 32.

As shown in FIG. 11B, the mounting portion 33 has a rod mounting portion 34 which can be moved parallel to the axis of the mounting portion 33 and an arrow direction II perpendicular to the arrow I. The bottom of the contact portion 31, namely, the offset (distance) from the position of the front tangent being contacted is scaled, for example, by millimeters and stamped. In the rod mounting portion 34, the offset from the front tangent can be adjusted by adjusting a screw 35. As indicated by an arrow III, the mounting angle can also be adjusted.

The rod in the marrow or a marker for the insertion position with the same shape as that of the rod in the marrow is attached to the rod mounting portion 34. The insertion point can be determined by measuring the distance from an approximated flat surface which has been calculated as described in (1) to the insertion point of the rod in the marrow in the intercondylar portion and by marking it.

An insertion inlet is formed by drilling the marked insertion position with a drill bit (not shown). Then, the rod in the marrow IM is inserted into the marrow of the femur EM from the insertion inlet at the pre-calculated depth.

Figure 12A:
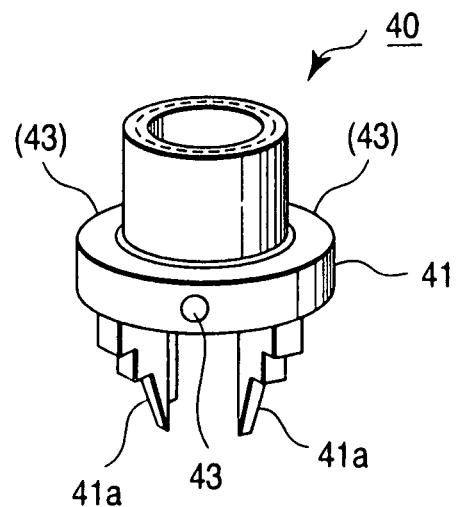
FIG. 12A is a perspective view illustrating the appearance structure of a rod keeper.

At this time, a rod keeper 40 as shown in FIG. 12A may be used so that the rod in the marrow IM is not moved carelessly.

Figure 12B:
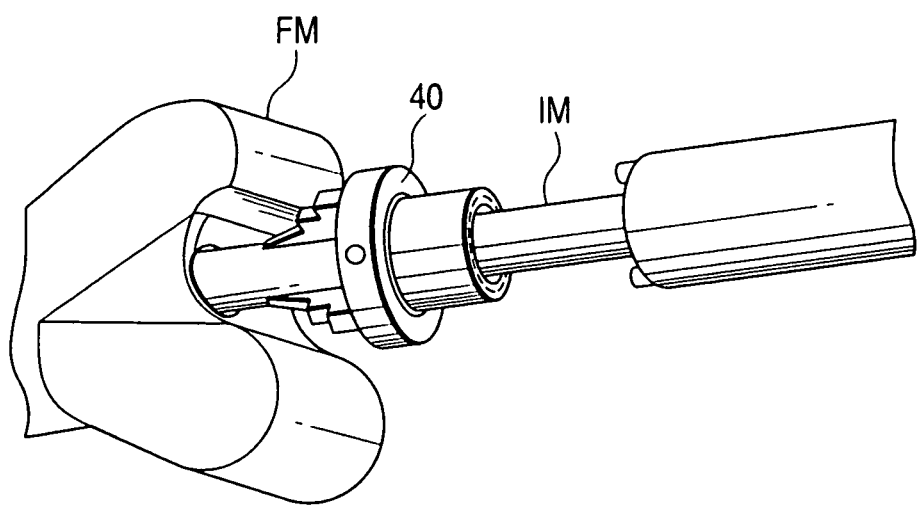
FIG. 12B is a diagram illustrating the rod keeper in the used state.

The rod keeper 40 shown in FIG. 12A has a two-stage cylindrical shape with different outer diameters. The central axis portion is hollow to pass the rod in the marrow IM. A spike 41a is protruded downward from the lower bottom side of a large diameter side cylindrical portion 41. As shown in FIG. 12B, the spike 41a is driven in the insertion inlet of the femur EM (shown as a three-dimensional model herein) in the state that the rod in the marrow IM is passed through.

A plurality of screw holes, for example, three screw holes 43 are passed through a small diameter side cylindrical portion 42 of the rod keeper 40 so as to form an equal central angle from the center of the axis position in the radial direction. As shown in FIG. 12B, screws (not shown) are threadably mounted on each of the screw holes 43 and thus the rod in the marrow IM inserted from the insertion inlet of the femur FM can be held without wobble.

Thereafter, a conventional jig for bone cutting (not shown) is attached to the rod in the marrow IM. At this time, the jig for bone cutting is previously adjusted to the valgus angle as described in (4) which has been previously calculated for the rod in the marrow IM. The horizontal axis of the flat surface portion which is referred to as a distal ablation paddle of the jig is matched with the X-axis of the rod in the marrow IM and the X-axis of the artificial joint CP. When the flat surface is matched with the distal bone cutting surface to be intended, the intended distal bone cutting is performed.

Figure 13A:
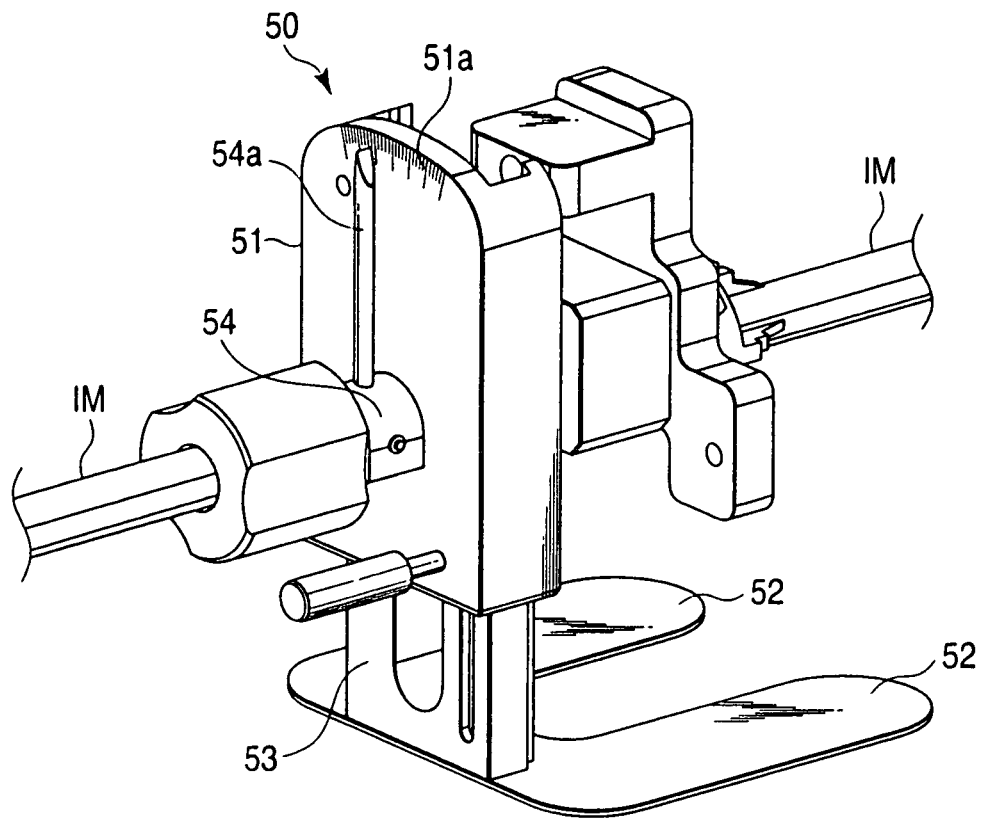
FIG. 13A is a perspective view illustrating the appearance structure of a jig for determining the rotation angle.
Figure 13B:
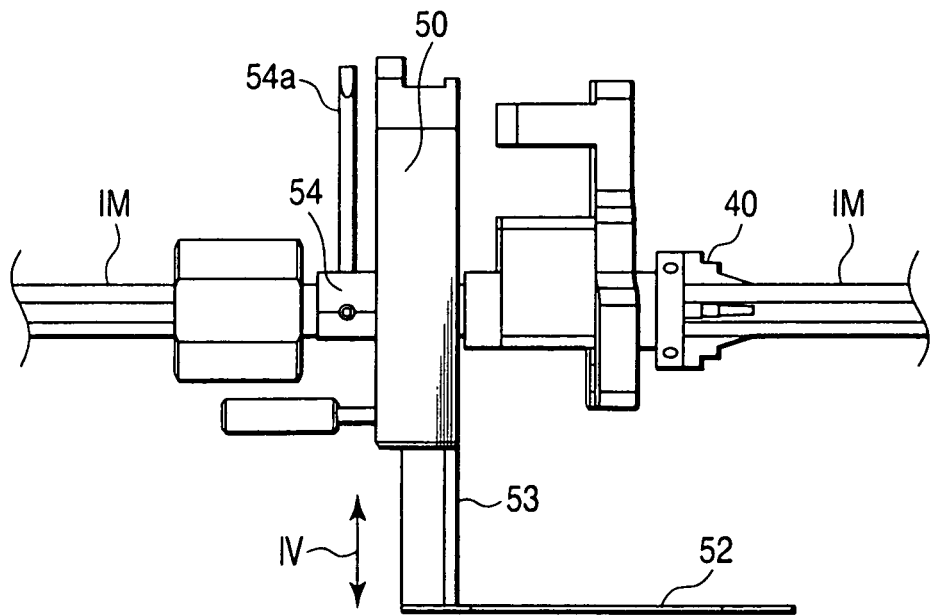
FIG. 13B is a side view illustrating the appearance structure of the jig for determining the rotation angle.

FIGS. 13A and 13B show the structure of a jig for determining the rotation angle 50 which is mounted from a distal position of the jig for bone cutting together with the rod keeper 40 and other jigs. FIG. 13A is a perspective view and FIG. 13B is a side view.

In the jig for determining the rotation angle 50, a pair of paddles 52 is provided on the lower end side of a mounting portion 51 which passes through the rod in the marrow IM so as to be integral with the connection portion 53. The paddles 52 contact the medial and lateral posterior condylar portions of the femur FM. As shown in FIG. 13B, the connection portion 53 is slidably attached to the mounting portion 51 so that the distance of the pair of paddles 52 with the rod axis portion can be adjusted as indicated by an arrow IV in the drawing.

A rotational portion 54 which is rotatably provided on the mounting portion 51 and is passed through the rod in the marrow IM is provided. The rotational portion 54 is located at the front side of the side of the mounting portion 51, a pointer 54a is radially attached to the rotational portion 54, and a scale 51a is formed at the side of the mounting portion 51.

The jig for determining the rotation angle 50 is mounted from the distal position of the jig for bone cutting. The angle of the rotational portion 54 is adjusted to the mounting portion 51 so that the angle between the jig for bone cutting and the jig for determining the rotation angle 50 is equal to the "posterior condylar tangent-artificial joint angle" calculated by the program for preoperative planning. Then, the rod in the marrow IM and the jig for bone cutting are rotated.

The rotation angle of the artificial joint CP is realized by this rotation. At this point, the condylar portion of the femur is drilled so that two points on the horizontal axis of the jig for bone cutting (matched with the X-axis of the artificial joint CP) becomes perpendicular to the flat surface of the jig and small bone holes are produced. Thereafter, the distal bone cutting is performed using conventional instrument. The rotation angle is determined in reference to two bone holes which have been previously made on the distal bone cutting surface and posterior bone cutting is performed.

However, in some cases, the cartilage may remain in the posterior condylar of the femur. Because of the uneven thickness, when the posterior condylar tangent is used to determine the rotation angle, the exact control may become difficult.

As another method for determining the rotation angle, the "front tangent-artificial joint angle" is used. A special jig for determining the rotation angle which measures how many degrees the front tangent is rotated about the rod axis from a more distal position of the jig for bone cutting is used.

FIGS. 14A and 14B show the structure of a jig for determining the rotation angle 60 which is mounted from a distal position of the jig for bone cutting together with the rod keeper 40 and other jigs. FIG. 14A is a perspective view and FIG. 14B is a side view.

In the jig for determining the rotation angle 60, the contact portion 64 is provided on the upper end side of a mounting portion 61 which passes through the rod in the marrow IM via a connection portion 62 and the arm portion 63. The contact portion 64 is the piece which contacts the front tangent as with the contact portion 31 of the target device 30 in FIG. 11.

As for the arm portion 63 in which the contact portion 61 is formed at the end part, the arm length (distance between the mounting portion 61 and the contact portion 64) is optionally variable for the connection portion 62 as indicated by an arrow V in FIG. 14B. In addition, the connection portion 62 is slidably attached to the mounting portion 61 so that the distance (height) with the rod axis portion can be adjusted as indicated by an arrow VI in the drawing.

A rotational portion 65 which is rotatably provided on the mounting portion 61 and is passed through the rod in the marrow IM is provided. The rotational portion 65 is located at the front side of the side of the mounting portion 61, a pointer 65*a* is radially attached to the rotational portion 65, and a scale 61*a* is formed at the side of the mounting portion 61.

When the jig for determining the rotation angle with such a structure is used, any effect of cartilage is not caused. The correct rotation angle of the jig for bone cutting is obtained by measuring how many degrees the front tangent exposed at the time of the operation is rotated about the rod axis and allowing the angle between the angle of the rotation and the front tangent of the jig for bone cutting to be equal to the "front tangent-artificial joint angle" obtained by the program for preoperative planning.

In this regard, the present invention is not to be construed as being limited to the embodiments. Various variations can be made in implementation without departing from the spirit of the invention. Further, the function to be performed in the embodiments may be carried out in all the possible appropriate combinations. Various stages are included in the embodiments and various inventions may be extracted from a plurality of the disclosed constituent features in an appropriate combination. For example, when the effect can be obtained even if some constituent features are deleted from all the constituent features shown in the embodiments, the structure from which these constituent features are deleted can be extracted as the invention.

What is claimed is:

1. An apparatus for preoperative planning of an artificial knee joint replacement operation, comprising:

means for selecting images which accepts selection of a plurality of preliminarily input three-dimensional images of a femur and a tibia constructed from two-dimensional tomographic images of the lower limb including the knee joint;

means for installing a femur side artificial joint which accepts selection of the artificial joint to be replaced and input of an installation position of the artificial joint to be replaced from the three-dimensional images of the knee joint of the femur obtained by the means for selecting the images, by using a plurality of preliminarily input three-dimensional images of the artificial joint;

means for installing a tibia side artificial joint which accepts selection of the artificial joint to be replaced and input of an installation position of the artificial joint to be replaced from the three-dimensional images of the knee joint of the tibia obtained by the means for selecting the images, by using a plurality of preliminarily input three-dimensional images of the artificial joint;

means for installing an alignment rod which, based on the artificial joint installed by the means for installing the femur side artificial joint, reference points of the knee joint, and preliminarily input three-dimensional images of an alignment rod in marrow inserted into the femur by the artificial knee joint replacement operation, accepts input of an installation position of the alignment rod in the marrow;

means for determining a first parameter which determines various parameters that can be directly measured from the knee joint including an adjustment value of a first jig to specify an insertion position, insertion orientation and insertion depth of the alignment rod in the marrow, based on the position of the alignment rod in the marrow installed by the means for installing the alignment rod relative to the three-dimensional images of the femur; and means for determining a second parameter which determines various parameters that can be directly measured from the knee joint including an adjustment value of a second jig to specify a position of a bone cutting surface at a jig for bone cutting mounted at the alignment rod in the marrow to cut bone and a rotation angle of the bone cutting surface, based on the installation position of the artificial joint installed by the means for installing the femur side artificial joint relative to the three dimensional images of the femur and the position of the alignment rod in the marrow installed by the means for installing the alignment rod relative to the three-dimensional images of the femur.

* * * * *